(12) United States Patent
Harriman et al.

(10) Patent No.: US 11,920,141 B2
(45) Date of Patent: Mar. 5, 2024

(54) GLUFOSINATE RESISTANCE CASSETTES AND PLANTS COMPRISING THE SAME

(71) Applicant: OMS INVESTMENTS, INC., Los Angeles, CA (US)

(72) Inventors: Robert Harriman, Delaware, OH (US); Rebecca Torisky, Marysville, OH (US); Lisa Lee, Marysville, OH (US)

(73) Assignee: OMS INVESTMENTS, INC., Los Angeles, CA (US)

( * ) Notice: Subject to any disclaimer, the term of this patent is extended or adjusted under 35 U.S.C. 154(b) by 0 days.

(21) Appl. No.: 17/484,977

(22) Filed: Sep. 24, 2021

(65) Prior Publication Data
US 2023/0094103 A1  Mar. 30, 2023

(51) Int. Cl.
*C12N 15/82* (2006.01)
*A01N 57/20* (2006.01)
*C12N 9/10* (2006.01)

(52) U.S. Cl.
CPC ......... *C12N 15/8277* (2013.01); *A01N 57/20* (2013.01); *C12N 9/1029* (2013.01); *C12N 15/8274* (2013.01); *C12Y 203/01183* (2013.01)

(58) Field of Classification Search
CPC .................................................. C12N 15/8274
See application file for complete search history.

(56) References Cited

U.S. PATENT DOCUMENTS

| | | | | |
|---|---|---|---|---|
| 5,077,399 | A * | 12/1991 | Brauer | C12N 9/1029 536/23.7 |
| 10,501,753 | B2 * | 12/2019 | Harriman | A01N 57/20 |
| 10,736,295 | B1 * | 8/2020 | Stanley | A01H 5/10 |
| 2009/0178164 | A1 * | 7/2009 | Ledeboer | A01H 5/12 800/320 |
| 2011/0107455 | A1 * | 5/2011 | Lira | C12N 15/8277 800/300 |

* cited by examiner

*Primary Examiner* — Mykola V. Kovalenko
(74) *Attorney, Agent, or Firm* — ArentFox Schiff LLP

(57) ABSTRACT

The present disclosure provides glufosinate-tolerant turfgrasses (e.g., Kentucky bluegrass), methods of making glufosinate-tolerant turfgrasses, and methods of controlling weeds in a field comprising glufosinate-tolerant turfgrasses by treating the field with an effective amount of an herbicide comprising glufosinate.

24 Claims, 2 Drawing Sheets
Specification includes a Sequence Listing.

SEQUENCE LISTING

<160> NUMBER OF SEQ ID NOS: 5

<210> SEQ ID NO 1
<211> LENGTH: 2440
<212> TYPE: DNA
<213> ORGANISM: Artificial Sequence
<220> FEATURE:
<223> OTHER INFORMATION: Expression casette for PAT Gene from
      Alcaligenes faecalis, optimized for Lolium perenne

<400> SEQUENCE: 1
ctgatgatta ttttgttgat catgattttc ttttggctat ttgattttt  gaaagatatt     60 tttttccctg ggaagacacc tatgggacga agatatattatg ttatatatat atatatat    120 atatcacatc agtctctgca caaagtgcat cctgggctgc ttcaattata aagccccatt    180

-continued

```
caccacattt gctagatagt cgaaaagcac catcaatatt gagcttcagg tattttggt      240
tgtgttgtgg ttggattgat tctaatatat accaaatcaa tataattcac taccaaaata     300
taccatagcc atcacaactt tattaatttt ggtagcttaa gatggtatat ataataacca     360
attaacaact gattctaatt ttactacggc ccagtatcta ccaatacaaa caacgagta      420
tgttttcttc cgtcgtaatc gtacacagta caaaaaaacc tggccagcct ttcttgggct     480
ggggctctct ttcgaaaggt cacaaaacgt acacggcagt aacgccgctt cgctgcgtgt     540
taacggccac caaccccgcc gtgagcaaac ggcatcagct ttccacctcc tcgatatctc     600
cgcggcgccg tctggacccg ccccttttcc gttcctttct ttccttctcg cgtttgcgtg     660
gtggggacgg actccccaaa ccgcctctcc ctctctttat ttgtctatat tctcactggg     720
ccccaccccac cgcaccccctg ggcccactca cgagtccccc cctccccacc tataaatacc   780
ccaccccctc ctcgcctctt cctccatcaa tcgaatcccc aaaatcgcag agaaaaaaaa     840
atctcccctc gaagcgaagc gtcgaatcgc cttctcaagt ctagatccgc cgccgccggt     900
aaccaccccg cccctctcct cttctcttct ccgtttttt tttccgtctc ggtctcgatc      960
tttggccttg gtagtttggg tgggcgagag gcggcttcgt gcgcgcccag atcggtgcgc    1020
gggaggggcg ggatctcgcg gctggggctc tcgccggcgt ggatccggcc cggatctcgc    1080
ggggaatggg gctctcggat gtagatctgc gatccgccgt tgttggggga gatgatgggg    1140
ggtttaaaat ttccgccatg ctaaacaaga tcaggaagag gggaaaaggg cactatggtt    1200
tatattttta tatatttctg ctgcttcgtc aggcttagat gtgctagatc tttcttctt     1260
cttttttgtgg gtagaatttg aatccctcag cattgttcat cggtagtttt tcttttcatg   1320
atttgtgaca aatgcagcct cgtgcggagc ttttttgtag gtagaaggga tccatgccgt    1380
cctcctcctc ccaccgtcc accccgacg cgccccagag ggtgggcgtg gagctggcga     1440
ggtgcgcgtg cacggtgagg gtggtgcgcg acgacgacct cccggccatc acggcgatct    1500
acgcccacca cgtgaggacc ggcaccgcca gcttcgagga ggtccccccg gacgacacgg    1560
agatgagggc ccgctgcgcc aaggtgctcg acgcgggcct gccctacctc gtggccgaga    1620
gggacggcaa gctgctgggc tacgcctacg ccacccacta caggccccgc tccgcgtacc    1680
gcttcaccct cgaggactcc gtgtacatcg ccccggacgc gatcggccag ggcgtgggca    1740
ggaccctcct cctcacccctg atcgcgaggt gcgaggcgg gccctggcgg cagctcatcg    1800
cgaacgtcgg ggactcgggg aacaccgcct ccctcggcct ccacgccgcc tgcggcttcg    1860
tccaggccgc cgtgctcaag tccgtgggct tcaagttcgg ccgctggatc gacaccgtgc    1920
tcatgcagag gccactgaac gccggcgaca cgacgctgcc cgagtgatga gagctcgaat    1980
tcagcttcat tgcaagctag ctcctcctgc agggcaggca tgtcgcacag caaatgggca    2040
tgaaaagttg aaggcgctcc agtcctccag cttgtgtagt acacagtagc aataaaacgt    2100
tagtgtttgt cctgtgccca tcctgtatta ttctgttcca gggttcacc tttatcgtca     2160
gtgtgtggtc aggtttcaac ccttctcaga caaccccct cccagaaaaa aaacaaagga     2220
agaagtttgt gtccaggttt cagaatcccc tgtctgtaat taccattttg catgacaata    2280
atgagatact gtagatatta ataatgttcc agaccttcaa ggcctccctc cctcgcaaat    2340
tgcagattta cttgaggtat cattcggtat tcacaaaatg taacgtaaat agtagtgatt    2400
aacactcgat taccagcgat aggcagtttg aataagacgg                          2440
```

<210> SEQ ID NO 2

<211> LENGTH: 2437
<212> TYPE: DNA
<213> ORGANISM: Artificial Sequence
<220> FEATURE:
<223> OTHER INFORMATION: Expression casette for PAT Gene from
      Alcaligenes faecalis, optimized for Triticum aestivum

<400> SEQUENCE: 2

```
ctgatgatta ttttgttgat catgattttc ttttggctat ttgatttttt gaaagatatt     60
tttttccctg ggaagacacc tatgggacga agatattatg ttatatatat atatatatat    120
atatcacatc agtctctgca caaagtgcat cctgggctgc ttcaattata aagccccatt    180
caccacattt gctagatagt cgaaaagcac catcaatatt gagcttcagg tatttttggt    240
tgtgttgtgg ttggattgat tctaatatat accaaatcaa tataattcac taccaaaata    300
taccatagcc atcacaactt tattaatttt ggtagcttaa gatggtatat ataataacca    360
attaacaact gattctaatt ttactacggc ccagtatcta ccaatacaaa acaacgagta    420
tgttttcttc cgtcgtaatc gtacacagta caaaaaaacc tggccagcct ttcttgggct    480
ggggctctct ttcgaaaggt cacaaaacgt acacggcagt aacgccgctt cgctgcgtgt    540
taacggccac caaccccgcc gtgagcaaac ggcatcagct ttccacctcc tcgatatctc    600
cgcggcgccg tctggacccg ccccctttcc gttcctttct ttccttctcg cgtttgcgtg    660
gtggggacgg actccccaaa ccgcctctcc ctctctttat ttgtctatat tctcactggg    720
ccccacccac cgcacccctg ggcccactca cgagtccccc cctccccacc tataaatacc    780
ccaccccctc ctcgcctctt cctccatcaa tcgaatcccc aaaatcgcag agaaaaaaaa    840
atctcccctc gaagcgaagc gtcgaatcgc cttctcaagt ctagatccgc cgccgccggt    900
aaccaccccg cccctctcct ctttctttct ccgttttttt tttccgtctc ggtctcgatc    960
tttggccttg gtagtttggg tgggcgagag gcggcttcgt gcgcgcccag atcggtgcgc   1020
gggaggggcg ggatctcgcg gctggggctc tcgccggcgt ggatccggcc cggatctcgc   1080
ggggaatggg gctctcggat gtagatctgc gatccgccgt tgttggggga gatgatgggg   1140
ggtttaaaat ttccgccatg ctaaacaaga tcaggaagag gggaaaaggg cactatggtt   1200
tatattttta tatatttctg ctgcttcgtc aggcttagat gtgctagatc tttctttctt   1260
ctttttgtgg gtagaatttg aatccctcag cattgttcat cggtagtttt tcttttcatg   1320
atttgtgaca aatgcagcct cgtgcggagc ttttttgtag gtagaaggga tccatgccat   1380
cctccagctc tcacccatcc actccagatg ctccacaacg cgtgggagtt gagcttgcta   1440
ggtgcgcttg caccgtgagg gttgtgaggg acgatgatct cccagccatc accgccatct   1500
acgcccatca tgttaggacc ggaaccgcct ccttcgagga agtgccacca gacgatactg   1560
agatgagagc caggtgcgcc aaggtgctcg atgccggact tccatacctt gttgctgagc   1620
gcgacggcaa gctcctcgga tacgcttacg ccactcacta caggccaagg tccgcctaca   1680
ggttcaccct cgaggactcc gtgtacattg ccccagatgc catcggccaa ggcgttggca   1740
ggactctcct cctcactctt atcgcgagat gcgaaggtgg accgtggcgc caacttatcg   1800
ccaacgtggg agattccggc aacaccgctt ctctcggact ccatgctgcc tgcggattcg   1860
ttcaagccgg cgtgctcaag tccgtgggct tcaagtttgg ccgctggatc gacaccgtgc   1920
tcatgcaaag gccactcaac gccggcgaca ctactcttcc agagtgagag ctcgaattca   1980
gcttcattgc aagctagctc ctcctgcagg gcaggcatgt cgcacagcaa atgggcatga   2040
aaagttgaag gcgctccagt cctccagctt gtgtagtaca cagtagcaat aaaacgttag   2100
```

```
tgtttgtcct gtgccatcc  tgtattattc tgttccaggg tttcaccttt atcgtcagtg    2160
tgtggtcagg tttcaaccct tctcagaaca accccctccc agaaaaaaaa caaaggaaga    2220
agtttgtgtc caggtttcag aatcccctgt ctgtaattac cattttgcat gacaataatg    2280
agatactgta gatattaata atgttccaga ccttcaaggc ctccctcct  cgcaaattgc    2340 agatttactt gaggtatcat tcggtattca caaaatgtaa cgtaaatagt agtgattaac    2400
actcgattac cagcgatagg cagtttgaat aagacgg                             2437
```

```
<210> SEQ ID NO 3
<211> LENGTH: 594
<212> TYPE: DNA
<213> ORGANISM: Artificial Sequence
<220> FEATURE:
<223> OTHER INFORMATION: Codon-optimized phosphinothricin
      N-acetyltransferase ("PAT") enzyme

<400> SEQUENCE: 3
atgccgtcct cctcctccca cccgtccacc ccgacgcgc  cccagagggt gggcgtggag     60
ctggcgaggt gcgcgtgcac ggtgagggtg gtgcgcgacg acgacctccc ggccatcacg    120
gcgatctacg cccaccacgt gaggaccggc accgccagct cgaggaggt  cccccccggac   180 gacacggaga tgagggcccg ctgcgccaag gtgctcgacg cgggcctgcc ctacctcgtg    240
gccgagaggg acggcaagct gctgggctac gcctacgcca cccactacag gccccgctcc    300
gcgtaccgct tcacccctcga ggactccgtg tacatcgccc cggacgcgat cggccagggc    360
gtgggcagga ccctcctcct caccctgatc gcgaggtgcg agggcgggcc ctggcggcag    420
ctcatcgcga acgtcgggga ctcggggaac accgcctccc tcggcctcca cgccgcctgc    480
ggcttcgtcc aggccggcgt gctcaagtcc gtgggcttca agttcggccg ctggatcgac    540
accgtgctca tgcagaggcc actgaacgcc ggcgacacga cgctgcccga gtga          594
```

```
<210> SEQ ID NO 4
<211> LENGTH: 594
<212> TYPE: DNA
<213> ORGANISM: Artificial Sequence
<220> FEATURE:
<223> OTHER INFORMATION: Codon-optimized phosphinothricin
      N-acetyltransferase ("PAT") enzyme

<400> SEQUENCE: 4
atgccatcct ccagctctca cccatccact ccagatgctc cacaacgcgt gggagttgag     60
cttgctaggt gcgcttgcac cgtgagggtt gtgagggacg atgatctccc agccatcacc    120
gccatctacg cccatcatgt taggaccgga accgcctcct cgaggaagt  gccaccagac    180 gatactgaga tgagagccag gtgcgccaag gtgctcgatg ccggacttcc ataccttgtt    240
gctgagcgcg acggcaagct cctcggatac gcttacgcca ctcactacag gccaaggtcc    300
gcctacaggt tcaccctcga ggactccgtg tacattgccc cagatgccat cggccaaggc    360
gttggcagga ctctcctcct cactcttatc gcgagatgcg aaggtggacc gtggcgccaa    420
cttatcgcca acgtgggaga ttccggcaac accgcttctc tcggactcca tgctgcctgc    480
ggattcgttc aagccggcgt gctcaagtcc gtgggcttca agtttggccg ctggatcgac    540
accgtgctca tgcaaaggcc actcaacgcc ggcgacacta ctcttcccga gtga          594
```

```
<210> SEQ ID NO 5
<211> LENGTH: 197
<212> TYPE: PRT
<213> ORGANISM: Alcalgenes faecalis
```

```
<400> SEQUENCE: 5

Met Pro Ser Ser Ser His Pro Ser Thr Pro Asp Ala Pro Gln Arg
1               5                   10                  15

Val Gly Val Glu Leu Ala Arg Cys Ala Cys Thr Val Arg Val Val Arg
                20                  25                  30

Asp Asp Asp Leu Pro Ala Ile Thr Ala Ile Tyr Ala His His Val Arg
            35                  40                  45

Thr Gly Thr Ala Ser Phe Glu Val Pro Pro Asp Thr Glu Met
        50                  55                  60

Arg Ala Arg Cys Ala Lys Val Leu Asp Ala Gly Leu Pro Tyr Leu Val
65                  70                  75                  80

Ala Glu Arg Asp Gly Lys Leu Leu Gly Tyr Ala Tyr Ala Thr His Tyr
                85                  90                  95

Arg Pro Arg Ser Ala Tyr Arg Phe Thr Leu Glu Asp Ser Val Tyr Ile
                100                 105                 110

Ala Pro Asp Ala Ile Gly Gln Gly Val Gly Arg Thr Leu Leu Leu Thr
            115                 120                 125

Leu Ile Ala Arg Cys Glu Gly Gly Pro Trp Arg Gln Leu Ile Ala Asn
130                 135                 140

Val Gly Asp Ser Gly Asn Thr Ala Ser Leu Gly Leu His Ala Ala Cys
145                 150                 155                 160

Gly Phe Val Gln Ala Gly Val Leu Lys Ser Val Gly Phe Lys Phe Gly
                165                 170                 175

Arg Trp Ile Asp Thr Val Leu Met Gln Arg Pro Leu Asn Ala Gly Asp
                180                 185                 190

Thr Thr Leu Pro Glu
            195
```

GLUFOSINATE RESISTANCE CASSETTES AND PLANTS COMPRISING THE SAME

INCORPORATION OF SEQUENCE LISTING

The sequence listing that is contained in the file named "Sequences.txt," which is 11 kilobytes in size, was created on Sep. 24, 2021, and is filed electronically herewith and incorporated herein by reference.

FIELD OF THE DISCLOSURE

The invention relates to the field of plant molecular biology. More specifically, the invention relates to glufosinate resistance cassettes that can be incorporated into a plant, e.g., in a turfgrass, grain crop, agricultural crop, ornamental flower, legume, fruit, vegetable, herb, perennial plant, or tree, to provide resistance to this herbicide.

BACKGROUND

Turfgrasses are a well-accepted and defined class of grasses that are natural or hybridized and are used extensively in landscaping, parks, golf courses, sports playing fields, lawn tennis courts, gardens, walkpaths and the like for their unique and individualized characteristics. Among the more common turfgrasses are bluegrass, rough bluegrass, ryegrass (e.g., perennial or annual), bahia grass, bermuda grass, hybrid bermuda grass, blue gramma grass, buffalo grass, carpet grass, centipede grass, creeping bentgrass, colonial bentgrass, fescue (e.g., fine, tall, needle-leaved, broad-leaved, etc.), kikuyu grass, orchard grass, quack grass, seashore *Paspalum*, St. Augustine grass, and zoysia grass.

The intended use and appearance are prime considerations for turfgrass. Ideally, the turf should be suitable for the use for which it is intended and aesthetically appealing. It should also be well-adapted to the environment where it will be planted. The control of weeds in turfgrass can be problematic. Annual grasses, such as crabgrass, foxtail, dallisgrass, and goosegrass must be controlled by use of a variety of herbicides including bensulide, dithiopyr, oxadiazon, fenoxaprop and prodiamine applied at specific rates, environmental conditions, and seasons. Results vary even when applied by experts.

2-Amino-4-[hydroxy(methylphosphonoyl)]butanoic acid, also known as glufosinate or phosphinothricin, is a well-known herbicide that has activity on a broad spectrum of plant species. Glufosinate is a glutamine synthetase inhibitor that binds to the glutamate site. Glufosinate-treated plants die due to a buildup of ammonia in the thylakoid lumen, leading to the uncoupling of photophosphorylation, followed by the production of reactive oxygen species, lipid peroxidation, and membrane destruction. Accordingly, glufosinate is useful as a broad spectrum herbicide. Plants comprising transgenes that confer glufosinate tolerance are known in the art. For example, U.S. Pat. No. 6,333,449 disclosed a transgenic rice variety that displayed glufosinate tolerance.

SUMMARY OF EXEMPLARY ASPECTS OF THE DISCLOSURE

In view of glufosinate's effectiveness as a broad spectrum herbicide, there exists a need in the art for glufosinate-tolerant varieties of agriculturally-significant plants. However, success in this area has been limited and there remains a need for other types of plants with resistance to this herbicide, e.g., grasses. To that end, the present disclosure provides glufosinate-tolerant turfgrasses (e.g., Kentucky bluegrass), methods of making glufosinate-tolerant turfgrasses, and methods of controlling weeds in a field comprising glufosinate-tolerant turfgrasses by treating the field with an effective amount of an herbicide comprising glufosinate.

In another general aspect, the disclosure provides nucleic acid molecules comprising nucleic acid sequences that can be incorporated into various turfgrasses and other plants to provide glufosinate tolerance. In some aspects, the nucleic acid sequence is a nucleic acid sequence selected from: a) SEQ ID NO: 1, SEQ ID NO: 2, or a nucleic acid sequence that shares at least 80% sequence identity with SEQ ID NOs: 1 or 2; b) SEQ ID NO: 3, SEQ ID NO: 4, or a nucleic acid sequence that shares at least 80% sequence identity with SEQ ID NOs: 3 or 4; wherein the nucleic acid sequence encodes a phosphinothricin N-acetyltransferase ("PAT") enzyme. In some aspects, the nucleic acid sequence may share at least 81%, 82%, 83%, 84%, 86%, 87%, 88%, 89%, 90%, 91%, 92%, 93%, 94%, 95%, 96%, 97%, 98%, or 99% sequence identity with any one of SEQ ID NOs: 1-4. In some aspects, the nucleic acid sequence comprises SEQ ID NOs: 3 or 4, operably linked to a heterologous promoter and/or one or more genetic elements that regulate transcription or translation (e.g., any 3'UTR or intron sequence described herein). In some aspects, the nucleic acid molecule is isolated. In others, it may be incorporated into the genomic DNA or a plasmid within the cell of a plant, plant cutting, root, seed, or any other portion or tissue of a plant described herein.

In some aspects, the nucleic acid sequence encodes a phosphinothricin N-acetyltransferase. The nucleic acid sequence may further comprise a promoter and one or more elements (e.g., introns or untranslated regions, "UTRs") that module or enhance expression of the phosphinothricin N-acetyltransferase. The nucleic acid may be structured as a cassette comprising a promoter, a phosphinothricin N-acetyltransferase, and one or more such UTRs. In some aspects, the nucleic acid sequence is provided as an isolated DNA molecule, whereas in others it may be incorporated into genomic or vector DNA (e.g., in one or more cells of a plant).

In another general aspect, the disclosure provides methods for producing a plant that tolerates application of glufosinate comprising sexually crossing a first parent comprising a nucleic acid which provides glufosinate tolerance, with a second parent which lacks the nucleic acid or glufosinate tolerance. In some aspects, the parents are grasses which may, e.g., be independently selected from Bahia grass, bent grass, Bermuda grass, Blue grama grass, Buffalo grass, centipedes grasses, Fescue grass (e.g., a needle-leaved Fescue grass, tall Fescue, or broad-leaved Fescue grass), Kentucky bluegrass, ryegrass (e.g., an annual ryegrass or a perennial ryegrass), seashore *Paspalum*, St. Augustine grass, or zoysiagrass.

In another general aspect, the disclosure provides recombinant seeds comprising any of the nucleic acid sequences described herein which provide glufosinate tolerance, as well as turfgrass stands, lawns, sports fields, or golf courses comprising grass produced using such seeds or which comprise any of the nucleic acid sequences described herein.

In another general aspect, the disclosure comprises a transgenic plant, or a part thereof, comprising a nucleic acid sequence selected from SEQ ID NOs: 1-4, or a nucleic acid sequence that shares at least 80% sequence identity with SEQ ID NOs: 1-4. In other aspects, the nucleic acid sequence may share at least 81%, 82%, 83%, 84%, 86%, 87%, 88%, 89%, 90%, 91%, 92%, 93%, 94%, 95%, 96%, 97%, 98%, or 99% sequence identity with any one of SEQ ID NOs: 1-4. In some aspects, the part of the recombinant plant is a cell, bulb, tuber, crown, stem, tiller, cuttings including un-rooted cuttings, rooted cutting, and callus cutting or callus-generated plantlet; apical meristem, pollen, ovule, flower, shoot, stolon, propagule, seed, runner, corm, rhizome, root, or leaf.

In some aspects, the plant may be a grass, grain crop, an agricultural crop, ornamental flower, legume, fruit, vegetable, herb, perennial plant, or tree. For example, the plant may be a grain crop. In another aspect, the grain crop may be barley, sorghum, millet, rice, canola, corn, oats, wheat, barley, or hops. In a further aspect, the plant may be soybean. In one aspect, the plant may be an ornamental flower. In another aspect, the flower may be an annual or perennial ornamental flower. In another aspect, the ornamental flower may be a *Geranium*, *Petunia*, or daffodil. In one aspect, the plant may be a legume. In one aspect, the legume may be alfalfa, clover, peas, beans, lentils, lupins, mesquite, carob, soybeans, peanuts, or tamarind. In one aspect, the plant may be a fruit. In another aspect, the fruit may be a grape, raspberry, blueberry, strawberry, blackberry, watermelon, apple, cherry, pear, orange, lemon, or pumpkin. In one aspect, the plant may be a vegetable. In another aspect, the vegetable may be asparagus, Brussels sprouts, cabbage, carrots, celery, chard, collard greens, endive, tomatoes, beans, peas, broccoli, cauliflower, bell pepper, eggplant, kale, lettuce, okra, onion, radish, spinach, peppers, broccoli, cucumber, zucchini, eggplant, beet, squash, beans, potato, or onion. In one aspect, the plant may be a herb. In another aspect, the herb may be anise, basil, caraway, cilantro, chamomile, dill, fennel, lavender, lemon grass, marjoram, oregano, parsley, rosemary, sage, thyme, or mint. In one aspect, the plant may be a root vegetable or a vine vegetable. In another embodiment, the root vegetable may be a turnip, potato, carrot, or beet. In another aspect, the vine vegetable may be a cucumber, pumpkin, squash, melon, or zucchini. In one aspect, the plant may be an agricultural crop. In another aspect, the agricultural crop may be cotton, corn, sugar cane, wheat, soybean, tobacco, or citrus. In one aspect, the plant may be an ornamental plant. In another aspect, the ornamental plant may be a *Geranium*, *Petunia*, *Impatien*, *Verbena*, *Dahlia*, pansy, *Vinca*, *Ipomoea*, *Lantana*, *Salvia*, snapdragon, *Scaevola*, *Torenia*, *Lobelia*, *Dipladenia*, *Calibrachoa*, *Asters*, *Agerantum*, *Phlox*, *Penstemon*, *Gaillardia*, *Zinnia*, *Coleus*, *Osteospermum*, *Gerbera*, *Begonia*, *Angelonia*, *Dianthus*, *Calendula*, *Campanula*, *Celosia*, *Portulaca*, *Viola*, or mum. In another aspect, the ornamental plant may be a variety of the *Vinca* genus. In another aspect, the ornamental plant may be a variety of the *Helianthus annuus* genus. In another aspect, the ornamental plant may be a variety of the impatients *Hawkeri* genus. In another aspect, the ornamental plant may be a variety of the lantana genus. In another aspect, the ornamental plant may be a variety of the *Mandevilla hydrida* genus. In another aspect, the ornamental plant may be a variety of the *Pelargonium* interspecific genus. In another aspect, the ornamental plant may be a variety of the *Pentas lanceolata* genus. In another aspect, the ornamental plant may be a variety of the *Petunia pendula* genus. In another aspect, the ornamental plant may be a variety of the *Rudbeckia* genus. In another aspect, the ornamental plant may be a variety of the *Tagetes erecta* genus. In another aspect, the ornamental plant may be a variety of the *Viola cornuta* genus. In another aspect, the ornamental plant may be a variety of the *Viola wittrockiana* genus. In another embodiment, the ornamental plant may be a variety of the *Zinnia* genus. In some aspects, the plant may be a variety of *Cannabis sativa* (e.g., hemp), including without limitation *C. sativa* L. subsp. *sativa* var. *sativa* or *C. sativa* subsp. *indica*.

In still further aspects, a recombinant glufosinate-tolerant plant, or part thereof, may comprise the nucleic acid sequence of any one of SEQ ID NOs: 1-4, or a nucleic acid sequence that shares at least 80%, 81%, 82%, 83%, 84%, 86%, 87%, 88%, 89%, 90%, 91%, 92%, 93%, 94%, 95%, 96%, 97%, 98%, or 99% sequence identity with any one of SEQ ID NOs: 1-4. In another embodiment, the part may be a cell, bulb, tuber, crown, stem, tiller, cuttings including un-rooted cuttings, rooted cutting, and callus cutting or callus-generated plantlet; apical meristem, pollen, ovule, flower, shoot, stolon, propagule, seed, runner, corm, rhizome, root, or leaf.

In another aspect, a method for controlling weeds in a field may comprise growing a seed from a plant comprising a) the nucleic acid sequence of any one of SEQ ID NOs: 1-4, or a nucleic acid sequence that shares at least 80%, 81%, 82%, 83%, 84%, 86%, 87%, 88%, 89%, 90%, 91%, 92%, 93%, 94%, 95%, 96%, 97%, 98%, or 99% sequence identity with any one of SEQ ID NOs: 1-4; and treating the field with an effective amount of an herbicide comprising glufosinate. In some aspects, such methods may comprise growing a seed from a plant that is engineered a PAT enzyme having the polypeptide sequence of SEQ ID NO: 5, or a PAT enzyme that shares at least 80%, 81%, 82%, 83%, 84%, 86%, 87%, 88%, 89%, 90%, 91%, 92%, 93%, 94%, 95%, 96%, 97%, 98%, or 99% sequence identity with SEQ ID NO: 5 and which retains the ability to acetylate the free amino group of glufosinate when expressed in the plant.

The foregoing and other aspects of the invention will become more apparent from the following detailed description and accompanying drawings.

DETAILED DESCRIPTION OF EXEMPLARY EMBODIMENTS

Figure 1:
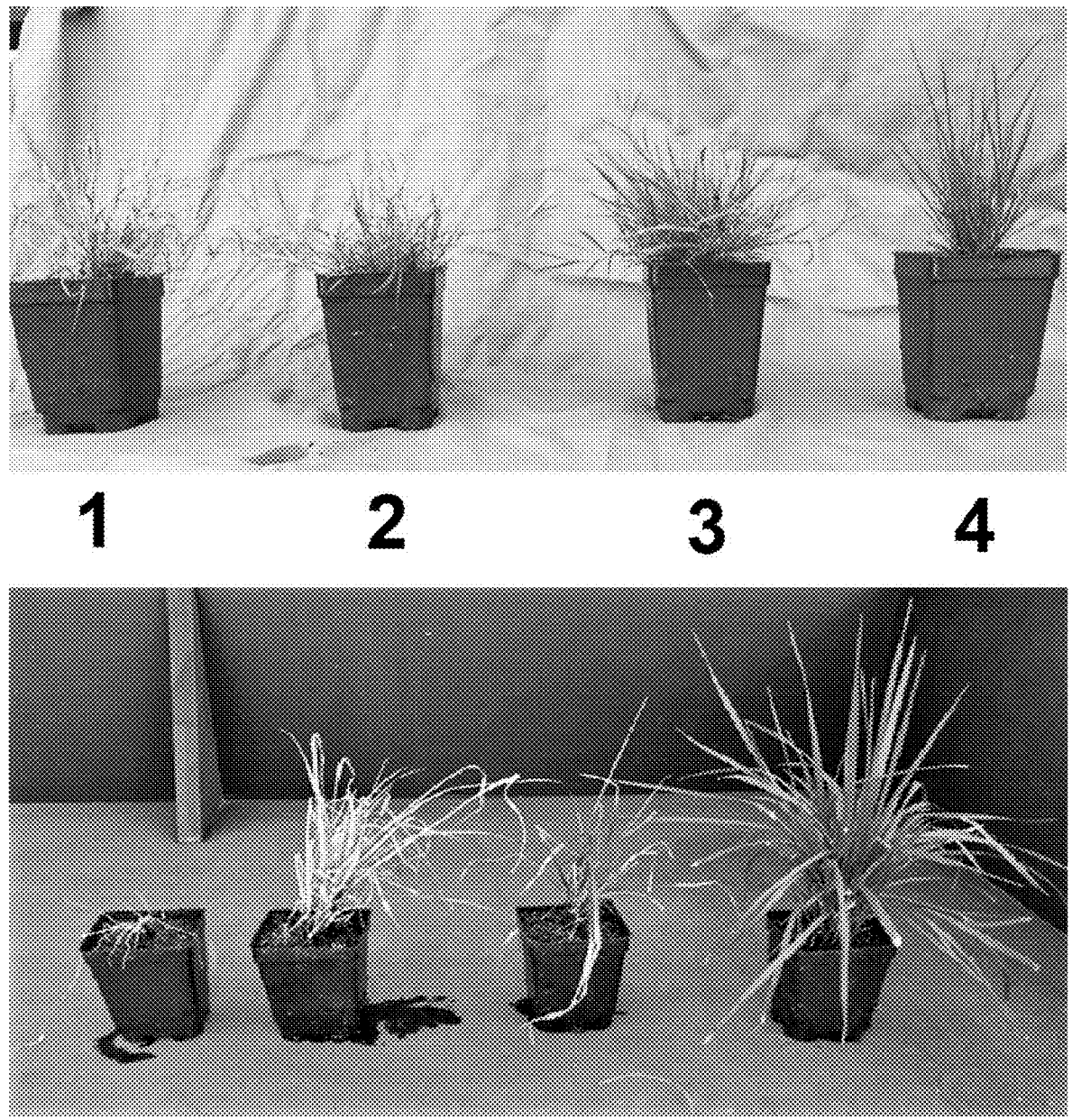
FIG. 1 is a photograph showing a grouping of Creeping Bentgrass (top) and Tall Fescue (bottom) plants transformed with a phosphinothricin N acetyltransferase (PAT) gene derived from *Alcalgenes faecalis*, *Bradyrhizobium japonicum*, or *Rhodopseudomonas palustris*. The plants were sprayed with the herbicide Glufosinate at 4 lb a.i. per acre. The grouping demonstrates the numerical scores assigned to the visual assessment of herbicide damage: 1=dead, 2=severe damage and dying, 3=slight damage and fully recoverable, 4=undamaged.

The present disclosure provides DNA sequences that can be incorporated into various plants (e.g., turfgrasses) to confer glufosinate tolerance. In some aspects, the DNA sequence is structured as a cassette comprising a gene encoding a phosphinothricin N-acetyltransferase, flanked by a promoter and optionally one or more elements (e.g., UTRs) that module expression of the phosphinothricin N-acetyltransferase, as exemplified by SEQ ID NOs.: 1 and 2. These cassettes may be integrated into the genomic DNA of a plant, or delivered using a vector, to produce a recombinant plant that displays resistance to glufosinate. Such plants may be treated with glufosinate during cultivation to reduce the presence of undesired weeds. In some aspects, the DNA sequence may comprise a codon-optimized version of a PAT gene, as exemplified by SEQ ID NOs: 3 or 4, alone or in combination with other elements such as a heterologous promoter or other regulatory elements described herein (e.g., a 3'UTR, or an intron sequence). The invention also provides plants, bulb, tuber, crown, stem, tiller, cuttings including un-rooted cuttings, rooted cuttings, and callus cuttings or callus-generated plantlets; apical meristems, pollen, ovule, flowers, shoots, stolons, propagules, seeds, runners, corms, rhizomes, roots, leaves, and plant material comprising any of the DNA sequences (e.g., glufosinate-tolerance cassettes) described herein.

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, Genes V, Oxford University Press: New York, 1994. The nomenclature for DNA bases as set forth at 37 CFR § 1.822 is used.

"Glufosinate" refers to 2-Amino-4-[hydroxy(methylphosphonoyl)]butanoic acid, also known as glufosinate or phosphinothricin. Commercial formulations of glufosinate marketed as an herbicide are typically provided as an ammonium salt.

"Conservative substitution," as used herein, refers broadly to the substitution of an amino acid by another amino acid of the same class, in which the classes are defined as follows: Nonpolar: A, V, L, I, P, M, F, W Uncharged polar: G, S, T, C, Y, N, Q Acidic: D, E Basic: K, R, H.

"Sequence identity," with regard to nucleotide sequences (DNA or RNA), as used herein, refers broadly to the number of positions with identical nucleotides divided by the number of nucleotides in the shorter of the two sequences. The alignment of the two nucleotide sequences is performed by the Wilbur and Lipmann algorithm (Wilbur and Lipmann, 1983, *Proc. Nat. Acad. Sci.* USA 80:726) using a window-size of 20 nucleotides, a word length of 4 nucleotides, and a gap penalty of 4. Computer-assisted analysis and interpretation of sequence data, including sequence alignment as described above, can, e.g., be conveniently performed using the sequence analysis software package of the Genetics Computer Group (GCG, University of Wisconsin Biotechnology center).

Glufosinate-Tolerance Cassettes

In one general aspect, the disclosure provides a cassette comprising a nucleic acid sequence which includes the sequence of a gene encoding a phosphinothricin N-acetyltransferase, flanked by a promoter and optionally one or more elements (e.g., UTRs) that module expression of the phosphinothricin N-acetyltransferase, as exemplified by SEQ ID NOs: 1 and 2. In some aspects, a cassette may comprise a nucleic acid sequence that shares at least 80% sequence identity with SEQ ID NOs: 1 or 2 (e.g., at least 81%, 82%, 83%, 84%, 86%, 87%, 88%, 89%, 90%, 91%, 92%, 93%, 94%, 95%, 96%, 97%, 98%, or 99% sequence identity). In some aspects, the cassette may comprise a codon-optimized nucleic acid that encodes a PAT gene, as exemplified by SEQ ID NOs: 3 or 4, alone or in combination with other elements such as a heterologous promoter or other regulatory elements described herein (e.g., a 3'UTR, or an intron sequence). In some aspects, a cassette may comprise a nucleotide sequence which encodes a polypeptide that shares at least 90%, 91%, 92%, 93%, 94%, 95%, 96%, 97%, 98%, or 99% with SEQ ID NO: 5 (i.e., the phosphinothricin N-acetyltransferase encoded by SEQ ID NOs: 3 and 4), and which retains the ability to acetylate the free amino group of glufosinate when the cassette is expressed in a plant (e.g., a turfgrass).

Generally, any promoter active in plant cells is suitable to express the nucleic acid molecules in plant cells. The promoter can be so chosen that the expression in the plants of the invention occurs constitutively or only in a particular tissue, at a particular time of plant development or at a time determined by external influences. The promoter may be homologous or heterologous to the plant. In some aspects, the promoter may further comprise or be adjacent to a heterologous intron sequence (e.g., a constitutive promoter element coupled to a heterologous intron sequence may enhance expression of an operably-linked protein coding gene).

Suitable promoters are for instance the promoter of 35S RNA of the Cauliflower Mosaic Virus (See, e.g., U.S. Pat. No. 5,352,605) and the ubiquitin-promoter (See, e.g., U.S. Pat. No. 5,614,399) which lend themselves to constitutive expression, the patatin gene promoter B33 (Rocha-Sosa, et al. *EMBO J.* 8 (1989), 23-29) which lends itself to a tuber-specific expression in potatoes or a promoter ensuring expression in photosynthetically active tissues only, for instance the ST-LS1 promoter (Stockhaus, et al. *Proc. Natl. Acad. Sci.* USA 84 (1987), 7943-7947; Stockhaus, et al. *EMBO, J.* 8 (1989) 2445-2451), the Ca/b-promoter (see for instance U.S. Pat. Nos. 5,656,496, 5,639,952, Bansal, et al. *Proc. Natl. Acad. Sci.* USA 89 (1992), 3654-3658) and the Rubisco SSU promoter (see for instance U.S. Pat. Nos. 5,034,322; 4,962,028) or the glutelin promoter from wheat which lends itself to endosperm-specific expression (HMW promoter) (Anderson, *Theoretical and Applied Genetics* 96, (1998), 568-576, Thomas, *Plant Cell* 2 (12), (1990), 1171-1180), the glutelin promoter from rice (Takaiwa, *Plant Mol. Biol.* 30(6) (1996), 1207-1221, Yoshihara, *FEBS Lett.* 383 (1996), 213-218, Yoshihara, *Plant and Cell Physiology* 37 (1996), 107-111), the shrunken promoter from maize (Maas, *EMBO J.* 8 (11) (1990), 3447-3452, Werr, *Mol. Gen. Genet.* 202(3) (1986), 471-475, Werr, *Mol. Gen. Genet.* 212(2), (1988), 342-350), the USP promoter, the phaseolin promoter (Sengupta-Gopalan, *Proc. Natl. Acad. Sci.* USA 82 (1985), 3320-3324, Bustos, *Plant Cell* 1 (9) (1989), 839-853) or promoters of zein genes from maize (Pedersen, et al. *Cell* 29 (1982), 1015-1026; Quatroccio, et al. *Plant Mol. Biol.* 15 (1990), 81-93). However, promoters which are only activated at a point in time determined by external influences can also be used (see for instance WO 93/07279). In this connection, promoters of heat shock proteins which permit simple induction may be of particular interest. Moreover, seed-specific promoters such as the USP promoter from *Vicia faba* which ensures a seed-specific expression in *Vicia faba* and other plants may be used (Fiedler, et al. *Plant Mol. Biol.* 22 (1993), 669-679; Baumlein, et al. *Mol. Gen. Genet.* 225 (1991), 459-467). Moreover, fruit-specific promoters, such as described in WO 91/01373 may be used. Shoot-preferred promoters may be used.

In some aspects, the cassette may also include at least a portion of the 3' UTR of *Zea mays* alcohol dehydrogenase gene (e.g., as exemplified by SEQ ID NOs.: 1 and 2). The cassette may comprise one or more restriction endonuclease recognition sites, e.g., between the promoter, enzyme, and any other elements (introns, UTRs, etc.)

Glufosinate-Tolerant Plants and Seeds

In another general aspect, the disclosure provides methods of producing glufosinate-tolerant plants (e.g., turfgrasses) comprising one or more of the cassettes described herein (e.g., the cassette represented by SEQ ID NOs.: 1 or 2). Such plants may display enhanced glufosinate tolerance as compared to corresponding wild-type plants. In some aspects, such recombinant plants may be produced by integrating the cassette into the genomic DNA of a plant, or transforming a plant with a vector that includes the cassette. In some aspects, a cassette described herein may be integrated into the germplasm of a plant (e.g., a plant seed, or a part of the plant from which new plants can be grown).

A plurality of techniques is available by which DNA can be inserted into a plant host cell. These techniques include the transformation of plant cells by T-DNA using *Agrobacterium tumefaciens* or *Agrobacterium rhizogenes* as a transforming agent, the fusion of protoplasts, injection, electroporation of DNA, insertion of DNA by the biolistic approach and other possibilities.

The use of *Agrobacterium*-mediated transformation of plant cells has been extensively investigated and sufficiently described in EP120516; Hoekema, In: *The Binary Plant Vector System*, Offsetdrukkerij Kanters B. V., Alblasserdam (1985), Chapter V; Fraley et al, *Crit. Rev. Plant Sci.* 4 (1993), 1-46 and An, et al. *EMBO J.* 4 (1985), 277-287. Regarding the transformation of potatoes see for instance Rocha-Sosa et al. (*EMBO J.* 8 (1989), 29-33).

The transformation of monocotyledonous plants by means of *Agrobacterium*-based vectors has also been described (Chan, et al. *Plant Mol. Biol.* 22 (1993), 491-506; Hiei, et al. *Plant J.* 6 (1994) 271-282; Deng et al, *Science in China* 33 (1990), 28-34; Wilmink et al, *Plant Cell Reports* 11 (1992), 76-80; May, et al. *Bio/Technology* 13 (1995), 486-492; Conner and Dormisse, *Int. J. Plant Sci.* 153 (1992), 550-555; Ritchie et al. *Transgenic Res.* 2 (1993), 252-265). An alternative system for transforming monocotyledonous plants is the transformation by the biolistic approach (Wan and Lemaux, *Plant Physiol.* 104 (1994), 37-48; Vasil, et al. *Bio/Technology* 11 (1993), 1553-1558; Ritala, et al. *Plant Mol. Biol.* 24 (1994) 317-325; Spencer, et al. *Theor. Appl. Genet.* 79 (1990), 625-631), protoplast transformation, electroporation of partially permeabilized cells, and insertion of DNA via glass fibers. The transformation of maize in particular has been repeatedly described in the literature (see for instance WO 95/06128, EP0513849, EP0465875, EP292435; Fromm et al, *Biotechnology* 8, (1990), 833-844; Gordon-Kamm, et al. *Plant Cell* 2, (1990), 603-618; Koziel, et al. *Biotechnology* 11 (1993), 194-200; Moroc, et al. *Theor. Appl. Genet.* 80, (1990), 721-726).

The successful transformation of other types of cereals has also been described for instance of barley (Wan and Lemaux, supra; Ritala, et al. supra, Krens et al. *Nature* 296 (1982), 72-74) and wheat (Nehra, et al. *Plant J.* 5 (1994), 285-297).

The series of methods consists in bombarding cells or protoplasts with particles to which DNA sequences are attached. One or more nucleic acids molecules comprising the sequence of SEQ ID NOs: 1-4, or a sequence sharing at least 80% sequence identity with any of these sequences, may be carried by the same particles or by different bombardments. Another method utilizes a chimeric gene inserted into an *Agrobacterium rhizogenes* Ri or *Agrobacterium tumefaciens* Ti plasmid. Other methods may be used, such as microinjection or electroporation. Persons skilled in the art will choose the appropriate method according to the nature of the plant, in particular its monocotyledonous or dicotyledonous character.

In some aspect, the recombinant plant is a grass, e.g., a Bahia grass, bent grass, Bermuda grass, Blue grama grass, Buffalo grass, centipedes grasses, Fescue grass (e.g., a needle-leaved Fescue grass, tall Fescue, or broad-leaved Fescue grass), Kentucky bluegrass, ryegrass (e.g., an annual ryegrass or a perennial ryegrass), seashore *Paspalum*, St. Augustine grass, or zoysiagrass.

In some aspects, the plant may be a grass, grain crop, an agricultural crop, ornamental flower, legume, fruit, vegetable, herb, ornamental flower, perennial plant, or tree. For example, the plant may be a grain crop. In another aspect, the grain crop may be barley, sorghum, millet, rice, canola, corn, oats, wheat, barley, or hops. In a further aspect, the plant may be soybean. In one aspect, the plant may be an ornamental flower. In another aspect, the flower may be an annual or perennial ornamental flower. In another aspect, the ornamental flower may be a *Geranium*, *Petunia*, or daffodil. In one aspect, the plant may be a legume. In one aspect, the legume may be alfalfa, clover, peas, beans, lentils, lupins, mesquite, carob, soybeans, peanuts, or tamarind. In one aspect, the plant may be a fruit. In another aspect, the fruit may be a grape, raspberry, blueberry, strawberry, blackberry, watermelon, apple, cherry, pear, orange, lemon, or pumpkin. In one aspect, the plant may be a vegetable. In another aspect, the vegetable may be asparagus, Brussels sprouts, cabbage, carrots, celery, chard, collard greens, endive, tomatoes, beans, peas, broccoli, cauliflower, bell pepper, eggplant, kale, lettuce, okra, onion, radish, spinach, peppers, broccoli, cucumber, zucchini, eggplant, beet, squash, beans, potato, or onion. In one aspect, the plant may be a herb. In another aspect, the herb may be anise, basil, caraway, cilantro, chamomile, dill, fennel, lavender, lemon grass, marjoram, oregano, parsley, rosemary, sage, thyme, or mint. In one aspect, the plant may be a root vegetable or a vine vegetable. In another embodiment, the root vegetable may be a turnip, potato, carrot, or beet. In another aspect, the vine vegetable may be a cucumber, pumpkin, squash, melon, or zucchini. In one aspect, the plant may be an agricultural crop. In another aspect, the agricultural crop may be cotton, corn, sugar cane, wheat, soybean, tobacco, or citrus. In one aspect, the plant may be an ornamental plant. In another aspect, the ornamental plant may be a *Geranium*, *Petunia*, *Impatien*, *Verbena*, *Dahlia*, pansy, *Vinca*, *Ipomoea*, *Lantana*, *Salvia*, snapdragon, *Scaevola*, *Torenia*, *Lobelia*, *Dipladenia*, *Calibrachoa*, *Asters*, *Agerantum*, *Phlox*, *Penstemon*, *Gaillardia*, *Zinnia*, *Coleus*, *Osteospermum*, *Gerbera*, *Begonia*, *Angelonia*, *Dianthus*, *Calendula*, *Campanula*, *Celosia*, *Portulaca*, *Viola*, or mum. In another aspect, the ornamental plant may be a variety of the *vinca* genus. In another aspect, the ornamental plant may be a variety of the *Helianthus annuus* genus. In another aspect, the ornamental plant may be a variety of the impatients *Hawkeri* genus. In another aspect, the ornamental plant may be a variety of the lantana genus. In another aspect, the ornamental plant may be a variety of the *Mandevilla hydrida* genus. In another aspect, the ornamental plant may be a variety of the *Pelargonium* interspecific genus. In another aspect, the ornamental plant may be a variety of the *Pentas lanceolata* genus. In another aspect, the ornamental plant may be a variety of the *Petunia pendula* genus. In another aspect, the ornamental plant may be a variety of the *Rudbeckia* genus. In another aspect, the ornamental plant may be a variety of the *Tagetes erecta* genus. In another aspect, the ornamental plant may be a variety of the *Viola cornuta* genus. In another aspect, the ornamental plant may be a variety of the *Viola wittrockiana* genus. In another embodiment, the ornamental plant may be a variety of the *Zinnia* genus. In some aspects, the plant may be a variety of *Cannabis sativa* (e.g., hemp), including without limitation *C. sativa* L. subsp. *sativa* var. *sativa* or *C. sativa* subsp. *indica*.

Recombinant glufosinate-tolerant plants may also be obtained by propagation of and/or breeding of plants comprising a cassette described herein (e.g., a plant grown from a seed deposited with the ATCC). Plant parts, such as bulb, tuber, crown, stem, tiller, cuttings including un-rooted cuttings, rooted cuttings, and callus cuttings or callus-generated plantlets; apical meristems, pollen, ovule, flowers, shoots, stolons, propagules, seeds, runners, corms, rhizomes, roots, or leaves which comprise any of the cassettes described herein are also encompassed herein.

Glufosinate-tolerant progeny may also be produced by a sexual outcross between a parental plant comprising a cassette described herein (e.g., an original transformant, or a plant grown from seed comprising the cassette), and itself or another parental plant that lacks glufosinate tolerance.

In one exemplary aspect, the invention provides for a method of producing a turfgrass (e.g., Kentucky bluegrass) plant or seed comprising crossing a grass comprising a glufosinate-tolerance cassette with a plant lacking glufosinate tolerance (or by selfing) and planting seed obtained from the cross or selfing, wherein the seed comprises a glufosinate-tolerance cassette. The method may also involve selecting progeny plants tolerant to glufosinate. The method may further include backcrossing (or selfing) the progeny plants with a plant comprising a glufosinate-tolerance cassette. The backcrossing or selfing step may be performed more than once. Plants and seeds (comprising a glufosinate-tolerance cassette) obtained from any of these methods are encompassed herein.

In another embodiment, a glufosinate tolerant, enhanced turfgrass-quality Kentucky bluegrass plant can be bred by first sexually crossing a parental Kentucky bluegrass plant, or other sexually compatible Kentucky bluegrass plant, grown from the transgenic Kentucky bluegrass plant derived from transformation with any of the plant expression cassettes described herein that tolerates application of glufosinate herbicide, and a second parental Kentucky bluegrass plant that lacks the tolerance to glufosinate herbicide, thereby producing a plurality of first progeny plants; and then selecting a first progeny plant that is tolerant to application of glufosinate herbicide (i.e, first glufosinate herbicide tolerant plant); and selfing or crossing the first progeny plant, thereby producing a plurality of second progeny plants; and then selecting from the second progeny plants, a glufosinate herbicide tolerant plant (i.e., second glufosinate herbicide tolerant plant). These steps can further include the back-crossing or crossing of the first glufosinate tolerant progeny plant or the second glufosinate tolerant progeny plant to the second parental Kentucky bluegrass plant or sexually compatible species or a third parental Kentucky bluegrass plant or sexually compatible species, thereby producing a Kentucky bluegrass plant that tolerates the application of glufosinate herbicide. Plants and seeds obtained from any of these methods are encompassed herein.

The present disclosure also provides plants obtainable by regeneration of transgenic plant cells comprising any of the glufosinate-tolerance cassettes described herein. Furthermore, plants containing the above-described transformed plant cells are contemplated herein. Transgenic plant cells can be regenerated to whole plants according to methods known to a person skilled in the art.

EXAMPLES

Example 1: Evaluation of Microbial PAT Gene Candidates

Several transgene expression cassettes were prepared for monocot plant codon-optimized sequences of four microbial PAT gene candidates, and introduced by standard microprojectile bombardment-mediated transformation into cell cultures of various grass species, including Creeping Bentgrass and Tall Fescue. The four PAT gene candidates used in this study were derived from *Alcalgenes faecalis, Corynebacterium glutamicum, Bradyrhizobium japonicum*, and *Rhodopseudomonas palustris*. These PAT gene candidates were tested alongside a commercially-used PAT gene derived from *Streptomyces hygroscopicus*, which was also monocot-optimized and introduced via a similar expression cassette.

The four PAT gene candidates were evaluated at the tissue culture stage and also in mature plants under greenhouse conditions.

Tissue Culture Study

For the tissue culture study, bombarded cells were grown/regenerated/rooted into plantlets on culture medium containing a Glufosinate-derived selection agent (Phosphinothricin or Bialaphos). The number of resistant individuals produced using each PAT gene candidate was recorded. A more effective PAT gene produces more resistant individuals per gram of bombarded cells. Table 1 below summarizes the yield of resistant events per bombarded sample of 0.3 g callus. The results are from two different grass species: Creeping Bentgrass (*Agrostis stolonifera*) and Tall Fescue (*Festuca arundinacea*).

TABLE 1

Summary of the yield of resistant events per bombarded sample of 0.3 g callus

| PAT gene source | Yield per sample Creeping Bentgrass | Yield per sample Tall Fescue |
|---|---|---|
| A. faecalis | 45.0 | 0.99 |
| C. glutamicum | 0.0 | 0.00 |
| B. japonicum | 28.0 | 0.00 |
| R. palustris | 22.0 | 0.57 |
| S. hygroscopicus | 26.0 | 2.30 |

As illustrated by Table 1, the *A. faecalis, B. japonicum*, and *R. palustris* PAT genes conferred resistance to glufosinate, with the *A. faecalis* PAT gene showing increased effectiveness. In particular, the *A faecalis* PAT gene produced the most resistance events per bombardment experiment among the PAT gene test candidates, in both Creeping Bentgrass and Tall Fescue. In contrast, the *C. glutamicum* PAT gene was found to be ineffective for producing transgenic plants.

Evaluation of the PAT Gene Candidates in Mature Plants

During the second phase of the experiment, mature plants were produced from rooted plantlets that were grown to maturity in soil, and spray-tested with Glufosinate (Finale™) at a 4× recommended rate of 4 lb of glufosinate per acre, and scored for resistance (1=dead, 4=undamaged). Survivors (scoring 3-4) were subjected to a Southern blot analysis for the number of transgene copies integrated into the genome.

FIG. 1 is a photograph showing a grouping of Creeping Bentgrass (top) and Tall Fescue (bottom) plants transformed with a PAT gene derived from *Alcalgenes faecalis*, *Bradyrhizobium japonicum*, or *Rhodopseudomonas palustris*. The plants were sprayed with the herbicide Glufosinate at 4 lb a.i. per acre. The grouping demonstrates the numerical scores assigned to the visual assessment of herbicide damage: 1=dead, 2=severe damage and dying, 3=slight damage and fully recoverable, and 4=undamaged.

Figure 2:
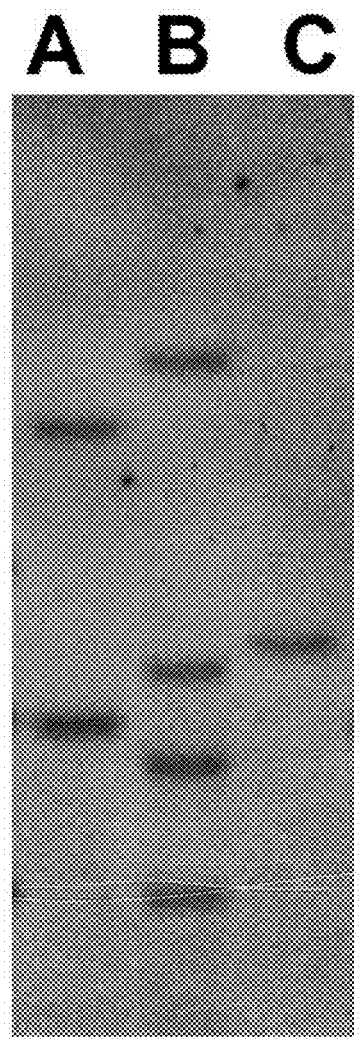
FIG. 2 is a photograph of a Southern blot used to confirm incorporation of the PAT gene in the transgenic group plantlets.

FIG. 2 is an annotated photograph of a Southern blot showing the incorporation of the candidate PAT genes into the tested plants. Based on band count, an estimate of the number of incorporated copies of the transgene can be determined. Column "A" identifies a plant with a low copy number (2 copies). Column "B" identifies a plant with a high copy number (4 copies). Column "C" identifies a plant with a single copy.

Table 2 below summarizes the effectiveness of transgene constructs derived from PAT gene candidates in Creeping Bentgrass, based on the percentage of transgenics which were protected by a single gene copy from 4× Glufosinate. Note that since the *C. glutamicum* PAT gene was ineffective for producing transgenics, as indicated above, no data was available for tests of mature plants modified with this transgene.

TABLE 2

Summary of the effectiveness of transgene constructs derived from PAT gene candidates in Creeping Bentgrass.

| PAT gene source | # CB unharmed survivors analyzed | % CB survivors with single gene copy |
| --- | --- | --- |
| A. faecalis | 198 | 53.0 |
| B. japonicum | 4 | 0.0 |
| R. palustris | 93 | 23.7 |

Table 3 below summarizes the effectiveness of transgene constructs derived from PAT gene candidates in Tall Fescue, based on the percentage of transgenics which were protected by a single gene copy from 4× Glufosinate.

TABLE 3

Summary of the effectiveness of transgene constructs derived from PAT gene candidates in Tall Fescue.

| PAT gene source | # TF unharmed survivors analyzed | % TF survivors with single gene copy |
| --- | --- | --- |
| A. faecalis | 37 | 62.2 |
| R. palustris | 14 | 14.3 |

The most effective transgene confers 4× Glufosinate survival from a single copy present in the genome. The highest percentage of survivors containing a single transgene copy based on Southern analysis indicates the most efficacious PAT gene candidate. The tissue culture and mature plant studies described herein confirm that PAT genes isolated from different microbial species exhibited varying degrees of efficacy when used as an glufosinate-resistant trait gene. The PAT gene from *A. faecalis* demonstrated the best and most consistent results among the four candidates, and rivaled the performance of the widely-used *S. hygroscopicus* PAT gene. In particular, the *A. faecalis* PAT gene produced the highest percentage of 4× Glufosinate-resistance events containing a single gene copy, among the four PAT gene candidates tested in this study.

SEQUENCE LISTING

SEQ ID NO: 1

```
CTGATGATTATTTTGTTGATCATGATTTTCTTTTGG
CTATTTGATTTTTTGAAAGATATTTTTTTCCCTGGG
AAGACACCTATGGGAGGAAGATATTATGTTATATAT
ATATATATATATATATCACATCAGTCTCTGCACAAA
GTGCATCCTGGGCTGCTTCAATTATAAAGCCCCATT
CACCACATTTGCTAGATAGTCGAAAAGCACCATCAA
TATTGAGCTTCAGGTATTTTTGGTTGTGTTGTGGTT
GGATTGATTCTAATATATACCAAATCAATATAATTC
ACTAGCAAAATATACCATAGCCATCACAACTTTATT
AATTTTGGTAGCTTAAGATGGTATATATAATAACCA
ATTAACAACTGATTCTAATTTTACTACGGCCCAGTA
TCTACCAATACAAAACAACGAGTATGTTTTCTTCCG
TCGTAATCGTACACAGTACAAAAAAACCTGGCCAGC
CTTTCTTGGGCTGGGGCTCTCTTTCGAAAGGTCACA
AAACGTACACGGCAGTAACGCCGCTTCGCTGCGTGT
TAACGGCCACCAACCCCGCCGTGAGCAAACGGCATC
AGCTTTCCACCTCCTCGATATCTCCGCGGCGCCGTC
TGGACCCGCCCCCTTTCCGTTCCTTTCTTTCCTTCT
CGCGTTTGCGTGGTGGGACGGACTCCCCAAACCGC
CTCTCCCTCTCTTTATTTGTCTATATTCTCACTGGG
CCCCACCCACCGCACCCCTGGGCCCACTCACGAGTC
CCCCCCTCCCCACCTATAAATACCCCACCCCCTCCT
CGCCTCTTCCTCCATCAATCGAATCCCCAAAATCGC
AGAGAAAAAAAATCTCCCCTCGAAGCGAAGCGTCG
AATCGCCTTCTCAAGTCTAGATCCGCCGCCGCCGGT
AACCACCCCGCCCCTCTCCTCTTTCTTTCTCCGTTT
TTTTTTTCCGTCTCGGTCTCGATCTTTGGCCTTGGT
AGTTTGGGTGGGCGAGAGGCGGCTTCGTGCGCGCCC
AGATCGGTGCGCGGGAGGGCGGGATCTCGCGGCTG
GGGCTCTCGCCGGCGTGGATCCGGCCCGGATCTCGC
GGGGAATGGGGCTCTCGGATGTAGATCTGCGATCCG
CCGTTGTTGGGGAGATGATGGGGGGTTTAAAATTT
CCGCCATGCTAAACAAGATCAGGAAGAGGGGAAAAG
GGCACTATGGTTTATATTTTTATATATTTCTGCTGC
TTCGTCAGGCTTAGATGTGCTAGATCTTTCTTTCTT
CTTTTTGTGGGTAGAATTTGAATCCCTCAGCATTGT
TCATCGGTAGTTTTTCTTTTCATGATTTGTGACAAA
TGCAGCCTCGTGCGGAGCTTTTTTGTAGGTAGAAGG
GATCCATGCCGTCCTCCTCCTCCCACCCGTCCACCC
CCGACGCGCCCCAGAGGGTGGGCGTGGAGCTGGCGA
```

-continued

GGTGCGCGTGCACGGTGAGGGTGGTGCGCGACGACG
ACCTCCCGGCCATCACGGCGATCTACGCCCACCACG
TGAGGACCGGCACCGCCAGCTTCGAGGAGGTCCCCC
CGGACGACACGGAGATGAGGGCCCGCTGCGCCAAGG
TGCTCGACGCGGGCCTGCCCTACCTCGTGGCCGAGA
GGGACGGCAAGCTGCTGGGCTACGCCTACGCCACCC
ACTACAGGCCCCGCTCCGCGTACCGCTTCACCCTCG
AGGACTCCGTGTACATCGCCCCGGACGCGATCGGCC
AGGGCGTGGGCAGGACCCTCCTCCTCACCCTGATCG
CGAGGTGCGAGGGCGGGCCCTGGCGGCAGCTCATCG
CGAACGTCGGGGACTCGGGGAACACCGCCTCCCTCG
GCCTCCACGCCGCCTGCGGCTTCGTCCAGGCCGGCG
TGCTCAAGTCCGTGGGCTTCAAGTTCGGCCGCTGGA
TCGACACCGTGCTCATGCAGAGGCCACTGAACGCCG
GCGACACGACGCTGCCCGAGTGATGAGAGCTCGAAT
TCAGCTTCATTGCAAGCTAGCTCCTCCTGCAGGGCA
GGCATGTCGCACAGCAAATGGGCATGAAAAGTTGAA
GGCGCTCCAGTCCTCCAGCTTGTGTAGTACACAGTA
GCAATAAAACGTTAGTGTTTGTCCTGTGCCCATCCT
GTATTATTCTGTTCCAGGGTTTCACCTTTATCGTCA
GTGTGTGGTCAGGTTTCAACCCTTCTCAGAACAACC
CCCTCCCAGAAAAAAAACAAAGGAAGAAGTTTGTGT
CCAGGTTTCAGAATCCCCTGTCTGTAATTACCATTT
TGCATGACAATAATGAGATACTGTAGATATTAATAA
TGTTCCAGACCTTCAAGGCCTCCCTCCCTCGCAAAT
TGCAGATTTACTTGAGGTATCATTCGGTATTCACAA
AATGTAACGTAAATAGTAGTGATTAACACTCGATTA
CCAGCGATAGGCAGTTTGAATAAGACGG

SEQ ID NO: 2
CTGATGATTATTTTGTTGATCATGATTTTCTTTTGG
CTATTTGATTTTTTGAAAGATATTTTTTTCCCTGGG
AAGACACCTATGGGAGGAAGATATTATG
TTATATATATATATATATATATCACATCAGTCTC
TGCACAAAGTGCATCCTGGGCTGCTTCAATTATAAA
GCCCCATTCACCACATTTGCTAGATAGTCGAAAAGC
ACCATCAATATTGAGCTTCAGGTATTTTTGGTTGTG
TTGTGGTTGGATTGATTCTAATATATACCAAATCAA
TATAATTCACTAGCAAAATATACCATAGCCATCACA
ACTTTATTAATTTTGGTAGCTTAAGATGGTATATAT
AATAACCAATTAACAACTGATTCTAATTTTACTACG
GCCCAGTATCTACCAATACAAAACAACGAGTATGTT

-continued

TTCTTCCGTCGTAATCGTACACAGTACAAAAAAACC
TGGCCAGCCTTTCTTGGGCTGGGGCTCTCTTTCGAA
AGGTCACAAAACGTACACGGCAGTAACGCCGCTTCG
CTGCGTGTTAACGGCCACCAACCCCGCCGTGAGCAA
ACGGCATCAGCTTTCCACCTCCTCGATATCTCCGCG
GCGCCGTCTGGACCCGCCCCCTTTCCGTTCCTTTCT
TTCCTTCTCGCGTTTGCGTGGTGGGGACGGACTCCC
CAAACCGCCTCTCCCTCTCTTTATTTGTCTATATTC
TCACTGGGCCCCACCCACCGCACCCCTGGGCCCACT
CACGAGTCCCCCCCTCCCCACCTATAAATACCCCAC
CCCCTCCTCGCCTCTTCCTCCATCAATCGAATCCCC
AAAATCGCAGAGAAAAAAAATCTCCCCTCGAAGCG
AAGCGTCGAATCGCCTTCTCAAGTCTAGATCCGCCG
CCGCCGGTAACCACCCCGCCCCTCTCCTCTTTCTTT
CTCCGTTTTTTTTTCCGTCTCGGTCTCGATCTTTG
GCCTTGGTAGTTTGGGTGGGCGAGAGGCGGCTTCGT
GCGCGCCCAGATCGGTGCGCGGGAGGGCGGGATCT
CGCGGCTGGGGCTCTCGCCGGCGTGGATCCGGCCCG
GATCTCGCGGGGAATGGGGCTCTCGGATGTAGATCT
GCGATCCGCCGTTGTTGGGGGAGATGATGGGGGGTT
TAAAATTTCCGCCATGCTAAACAAGATCAGGAAGAG
GGGAAAAGGGCACTATGGTTTATATTTTTATATATT
TCTGCTGCTTCGTCAGGCTTAGATGTGCTAGATCTT
TCTTTCTTCTTTTTGTGGGTAGAATTTGAATCCCTC
AGCATTGTTCATCGGTAGTTTTTCTTTTCATGATTT
GTGACAAATGCAGCCTCGTGCGGAGCTTTTTTGTAG
GTAGAAGGGATCCATGCCATCCTCCAGCTCTCACCC
ATCCACTCCAGATGCTCCACAACGCGTGGGAGTTGA
GCTTGCTAGGTGCGCTTGCACCGTGAGGGTTGTGAG
GGACGATGATCTCCCAGCCATCACCGCCATCTACGC
CCATCATGTTAGGACCGGAACCGCCTCCTTCGAGGA
AGTGCCACCAGACGATACTGAGATGAGAGCCAGGTG
CGCCAAGGTGCTCGATGCCGGACTTCCATACCTTGT
TGCTGAGCGCGACGGCAAGCTCCTCGGATACGCTTA
CGCCACTCACTACAGGCCAAGGTCCGCCTACAGGTT
CACCCTCGAGGACTCCGTGTACATTGCCCCAGATGC
CATCGGCCAAGGCGTTGGCAGGACTCTCCTCCTCAC
TCTTATCGCGAGATGCGAAGGTGGACCGTGGCGCCA
ACTTATCGCCAACGTGGGAGATTCCGGCAACACCGC
TTCTCTCGGACTCCATGCTGCCTGCGGATTCGTTCA

-continued
```
AGCCGGCGTGCTCAAGTCCGTGGGCTTCAAGTTTGG

CCGCTGGATCGACACCGTGCTCATGCAAAGGCCACT

CAACGCCGGCGACACTACTCTTCCAGAGTGAGAGCT

CGAATTCAGCTTCATTGCAAGCTAGCTCCTCCTGCA

GGGCAGGCATGTCGCACAGCAAATGGGCATGAAAAG

TTGAAGGCGCTCCAGTCCTCCAGCTTGTGTAGTACA

CAGTAGCAATAAAACGTTAGTGTTTGTCCTGTGCCC

ATCCTGTATTATTCTGTTCCAGGGTTTCACCTTTAT

CGTCAGTGTGTGGTCAGGTTTCAACCCTTCTCAGAA

CAACCCCCTCCCAGAAAAAAAACAAAGGAAGAAGTT

TGTGTCCAGGTTTCAGAATCCCTGTCTGTAATTAC

CATTTTGCATGACAATAATGAGATACTGTAGATATT

AATAATGTTCCAGACCTTCAAGGCCTCCCTCCCTCG

CAAATTGCAGATTTACTTGAGGTATCATTCGGTATT

CACAAAATGTAACGTAAATAGTAGTGATTAACACTC

GATTACCAGCGATAGGCAGTTTGAATAAGACGG
```

SEQ ID NO: 3
```
ATGCCGTCCTCCTCCTCCCACCCGTCCACCCCCGAC

GCGCCCCAGAGGGTGGGCGTGGAGCTGGCGAGGTGC

GCGTGCACGGTGAGGGTGGTGCGCGACGACGACCTC

CCGGCCATCACGGCGATCTACGCCCACCACGTGAGG

ACCGGCACCGCCAGCTTCGAGGAGGTCCCCCCGGAC

GACACGGAGATGAGGGCCCGCTGCGCCAAGGTGCTC

GACGCGGGCCTGCCCTACCTCGTGGCCGAGAGGGAC

GGCAAGCTGCTGGGCTACGCCTACGCCACCCACTAC

AGGCCCCGCTCCGCGTACCGCTTCACCCTCGAGGAC

TCCGTGTACATCGCCCCGGACGCGATCGGCCAGGGC

GTGGGCAGGACCCTCCTCCTCACCCTGATCGCGAGG

TGCGAGGGCGGGCCCTGGCGGCAGCTCATCGCGAAC
```

-continued
```
GTCGGGGACTCGGGGAACACCGCCTCCCTCGGCCTC

CACGCCGCCTGCGGCTTCGTCCAGGCCGGCGTGCTC

AAGTCCGTGGGCTTCAAGTTCGGCCGCTGGATCGAC

ACCGTGCTCATGCAGAGGCCACTGAACGCCGGCGAC

ACGACGCTGCCCGAGTGA
```

SEQ ID NO: 4
```
ATGCCATCCTCCAGCTCTCACCCATCCACTCCAGAT

GCTCCACAACGCGTGGGAGTTGAGCTTGCTAGGTGC

GCTTGCACCGTGAGGGTTGTGAGGGACGATGATCTC

CCAGCCATCACCGCCATCTACGCCCATCATGTTAGG

ACCGGAACCGCCTCCTTCGAGGAAGTGCCACCAGAC

GATACTGAGATGAGAGCCAGGTGCGCCAAGGTGCTC

GATGCCGGACTTCCATACCTTGTTGCTGAGCGCGAC

GGCAAGCTCCTCGGATACGCTTACGCCACTCACTAC

AGGCCAAGGTCCGCCTACAGGTTCACCCTCGAGGAC

TCCGTGTACATTGCCCCAGATGCCATCGGCCAAGGC

GTTGGCAGGACTCTCCTCCTCACTCTTATCGCGAGA

TGCGAAGGTGGACCGTGGCGCCAACTTATCGCCAAC

GTGGGAGATTCCGGCAACACCGCTTCTCTCGGACTC

CATGCTGCCTGCGGATTCGTTCAAGCCGGCGTGCTC

AAGTCCGTGGGCTTCAAGTTTGGCCGCTGGATCGAC

ACCGTGCTCATGCAAAGGCCACTCAACGCCGGCGAC

ACTACTCTTCCAGAGTGA
```

SEQ ID NO: 5
```
MPSSSSHPSTPDAPQRVGVELARCACTVRVVRDDDL

PAITAIYAHHVRTGTASFEEVPPDDTEMRARCAKVL

DAGLPYLVAERDGKLLGYAYATHYRPRSAYRFTLED

SVYIAPDAIGQGVGRTLLLTLIARCEGGPWRQLIAN

VGDSGNTASLGLHAACGFVQAGVLKSVGFKFGRWID

TVLMQRPLNAGDTTLPE
```

---

The invention claimed is:

1. A nucleic acid molecule comprising a nucleic acid sequence selected from:
SEQ ID NO: 1, a nucleic acid molecule having at least 97% sequence identity to SEQ ID NO: 1, SEQ ID NO: 2, or a nucleic acid molecule having at least 97% sequence identity to SEQ ID NO: 2,
wherein the nucleic acid sequence encodes a phosphinothricin N-acetyltransferase ("PAT") enzyme.

2. The nucleic acid molecule of claim 1, wherein the nucleic acid sequence comprises SEQ ID NOs: 3 or 4.

3. A recombinant plant, or a plant part thereof, comprising the nucleic acid molecule of claim 1.

4. The recombinant plant of claim 3, wherein the nucleic acid molecule is integrated into the genome of the plant.

5. The recombinant plant of claim 3, wherein the PAT enzyme is expressed at a level that provides glufosinate tolerance.

6. The recombinant plant of claim 3, wherein the plant is a grass.

7. The recombinant plant of claim 6, wherein the grass is Bahia grass, bent grass, Bermuda grass, Blue grama grass, Buffalo grass, centipede grass, Fescue grass, Kentucky bluegrass, ryegrass, seashore *paspalum*, St. Augustine grass, or zoysiagrass.

8. The recombinant plant of claim 7, wherein the Fescue grass is needle-leaved Fescue grass, tall Fescue grass, or broad-leaved Fescue grass; or the ryegrass is an annual ryegrass or a perennial ryegrass.

9. A recombinant seed comprising the nucleic acid molecule of claim 1.

10. The recombinant seed of claim 9, wherein the seed is a grass seed.

11. The recombinant seed of claim 10, wherein the grass is Bahia grass, bent grass, Bermuda grass, Blue grama grass, Buffalo grass, centipede grass, Fescue grass, Kentucky bluegrass, ryegrass, seashore *paspalum*, St. Augustine grass, or zoysiagrass.

12. An expression vector comprising the nucleic acid molecule of claim 1.

13. A turfgrass stand, lawn, sports field, or golf course comprising a turfgrass plant comprising the nucleic acid molecule of claim 1.

14. The recombinant plant of claim 3, wherein the plant is:
a) a grass, grain crop, an agricultural crop, legume, fruit, vegetable, herb, ornamental flower, perennial plant, or tree;
b) a grain crop comprising barley, sorghum, millet, rice, canola, corn, oats, wheat, barley, or hops;
c) a vegetable comprising asparagus, Brussels sprouts, cabbage, carrots, celery, chard, collard greens, endive, tomatoes, beans, peas, broccoli, cauliflower, bell pepper, eggplant, kale, lettuce, okra, onion, radish, spinach, peppers, broccoli, cucumber, zucchini, eggplant, beet, squash, beans, potato, or onion; or
d) an agricultural crop comprising cotton, corn, sugar cane, wheat, soybean, tobacco, or citrus.

15. The plant part of claim 3, wherein the part is a cell, bulb, tuber, crown, stem, tiller, unrooted cutting, rooted cutting, callus, callus generated plantlet, apical meristem, pollen, ovule, flower, shoot, stolon, propagule, seed, runner, corm, rhizome, root, or leaf.

16. The recombinant plant of claim 3, wherein the plant comprises:
 a) a variety of *Cannabis sativa*;
 b) *C. sativa* L. subsp. *sativa* var. *sativa*; or
 c) *C. sativa* subsp.

17. The nucleic acid molecule of claim 1, wherein the nucleic acid sequence comprises SEQ ID NO: 1.

18. The nucleic acid molecule of claim 1, wherein the nucleic acid sequence has at least 97% sequence identity to SEQ ID NO: 1.

19. The nucleic acid molecule of claim 1, wherein the nucleic acid sequence comprises SEQ ID NO: 2.

20. The nucleic acid molecule of claim 1, wherein the nucleic acid sequence has at least 97% sequence identity to SEQ ID NO: 2.

21. The nucleic acid molecule of claim 1, wherein the nucleic acid sequence has at least 98% sequence identity to SEQ ID NO: 1.

22. The nucleic acid molecule of claim 1, wherein the nucleic acid sequence has at least 99% sequence identity to SEQ ID NO: 1.

23. The nucleic acid molecule of claim 1, wherein the nucleic acid sequence has at least 98% sequence identity with SEQ ID NO: 2.

24. The nucleic acid molecule of claim 1, wherein the nucleic acid sequence has at least 99% sequence identity to SEQ ID NO: 2.

\* \* \* \* \*